United States Patent [19]

Burgess et al.

[11] Patent Number: 5,078,854
[45] Date of Patent: Jan. 7, 1992

[54] POLAROGRAPHIC CHEMICAL SENSOR WITH EXTERNAL REFERENCE ELECTRODE

[75] Inventors: Bruce Burgess; Mark Meyerhoff; Peter H. Burleigh, all of Ann Arbor; John Ellison, Whitmore Lake; Christine A. Smith, Ann Arbor, all of Mich.

[73] Assignee: Mallinckrodt Sensor Systems, Inc., Ann Arbor, Mich.

[21] Appl. No.: 468,277

[22] Filed: Jan. 22, 1990

[51] Int. Cl.$^5$ .................. G01N 27/26; G01N 27/30
[52] U.S. Cl. .................. 204/403; 204/409; 204/416; 204/418; 435/817
[58] Field of Search .......... 204/409, 415, 403, 416, 204/418; 435/817, 291, 288

[56] References Cited

U.S. PATENT DOCUMENTS

| | | | |
|---|---|---|---|
| 3,838,033 | 9/1974 | Mindt et al. | 204/415 X |
| 3,840,452 | 10/1974 | Baum et al. | 204/418 |
| 3,855,097 | 12/1974 | Sharp et al. | 204/418 X |
| 3,857,777 | 12/1974 | Guilbault et al. | 204/418 X |
| 3,932,233 | 1/1976 | Ruzicka et al. | 204/418 |
| 3,948,745 | 4/1976 | Guilbault et al. | 204/415 X |
| 3,957,613 | 5/1976 | Macur | 204/415 X |
| 4,148,305 | 4/1979 | Reichenberger | 204/415 X |
| 4,168,219 | 9/1979 | Hiiro et al. | 204/418 |
| 4,224,125 | 9/1980 | Nakamura et al. | 204/415 X |
| 4,654,127 | 3/1987 | Baker et al. | 204/409 X |
| 4,818,361 | 4/1989 | Burgess et al. | 204/406 |
| 4,820,399 | 4/1989 | Senda et al. | 204/403 |
| 4,832,797 | 5/1989 | Vadgama et al. | 204/403 |
| 4,871,439 | 10/1989 | Enzer et al. | 204/401 |

*Primary Examiner*—John F. Niebling
*Assistant Examiner*—William T. Leader
*Attorney, Agent, or Firm*—Krass & Young

[57] ABSTRACT

An electroanalytical electrode assembly includes an electrically conductive working electrode having a body of electrolyte material thereupon and separated from the analytical environment by a hydrophobic membrane. The membrane has an electrical conductivity greater than the electrical conductivity of the remainder of the measuring circuit and is selectably permeable for a preselected and ionic species, so as to provide a stable membrane potential. Use of an assembly of this type allows for placement of a reference electrode external of the membrane.

23 Claims, 3 Drawing Sheets

POLAROGRAPHIC CHEMICAL SENSOR WITH EXTERNAL REFERENCE ELECTRODE

FIELD OF THE INVENTION

This invention relates generally to electrochemical analyses and particularly to analytical apparatus and methods relying upon measurement of the current flow or the potential differences between a pair of electrodes for determination of the concentration or activity of chemical species dissolved in a fluid. Most particularly, the present invention relates to a polarographic amperometric sensor having a hydrophobic membrane and an external reference electrode.

BACKGROUND OF THE INVENTION

There are a number of electrochemical analytical techniques which may be employed for determining the presence and/or concentrations of various chemical species. Electroanalytical techniques have enjoyed particular success in the measurement of the concentrations or activities of gaseous or ionic species dissolved in liquids, and have been applied inter alia, to the analysis of blood and other biological fluids. Polarographic analyses are particularly well-suited for the determination of a variety of dissolved species and in general involve the immersion of a pair of electrodes into a sample containing the analyte. One of the electrodes is termed the working electrode and a second is a reference electrode. A preselected potential is applied to the working electrode relative to the reference electrode and this potential causes a change in the oxidation state of a given species of interest at the electrode/sample interface and a transfer of electrons thereacross. The transfer of electrons results in a flow of current which is proportional to the concentration or activity of the target species at the surface of the working electrode. By measuring the amount of current flowing between the two electrodes, the concentration of the target species may be determined accurately.

Polarographic methods may be advantageously employed for the determination of the concentration of dissolved oxygen in a fluid sample. In such instance, the measuring electrode is generally fabricated from a noble metal such as gold or platinum, selected for its nonreactivity with the oxygen. The reference electrode is typically metal, with a metal halide coating formed thereupon, such as silver with a surface coating of silver chloride. It could also be a composite material containing a metal halide, such as a silver chloride pellet. Application of a negative potential to the working electrode (e.g., a Pt electrode) causes a flow of electrons from the electrode to the oxygen atoms which results in the reduction of oxygen to $H_2O_2$ and/or OH at the electrode surface. This flow of electrons or current flow can be measured in an external circuit interconnecting the two electrodes, and such flow is proportional to the rate of oxygen diffusion to the working electrode, which in turn is proportional to the concentration of oxygen. By appropriate choice of electrode material and applied potential, analyses of other species including other dissolved gases, neutral species and ions may be similarly accomplished. In some instances, the electrode material itself is directly reactive with the dissolved species to effect a transfer of electrons in the absence of an applied external potential; however, the principles generally remain the same and this potential (or current flow resultant therefrom) is measured.

In most practical applications, the afore-described electrodes are both separated from the sample fluid by means of a membrane preferably having a selective permeability. The membrane screens out interfering species present in the sample and serves to provide a fixed analytical environment in which the electrodes operate. U.S. patent application Ser. No. 148,155, now U.S. Pat. No. 4,871,439, which is assigned to the assignee of the present invention discloses one such prior art electrode assembly. Referring now to FIG. 1, there is shown a prior art polarographic electrode assembly including a flow channel 10 configured to carry a stream of sample fluid therethrough. The electrode assembly further includes a working electrode 12 formed from a length of platinum wire and a reference electrode 14 comprised of a length of silver wire having a silver chloride coating 11 upon at least the active face thereof. The working electrode 12 and reference electrode 14 are in electrical communication via a body of electrolyte material 11 which is separated from the fluid in the fluid flow channel 10 by a membrane 19. The membrane 19 is a hydrophobic membrane, typically formed of material such as poly(vinyl chloride), and having a permeability to oxygen and water.

While electrode assemblies of this type have been found to provide excellent results in terms of accuracy and reliability it has been recognized that many advantages would attend upon the placement of the reference electrode outside of the membrane in the sample fluid. Fabrication of the electrode assembly would be simplified insofar as the need for the common electrolyte layer (17 in FIG. 1) establishing a conductive bridge between the two electrodes would be eliminated; hence a smaller, thinner electrolyte layer could be readily utilized. It has been found that problems arise in the preparation and use of the relatively thick electrolyte layer necessitated by the presence of the reference electrode beneath the membrane. The hydrophobic membranes are prone to manifest openings therethrough when deposited atop the irregular geometry of the thick electrolyte layers. Hence, thicker, difficult to prepare membranes must be employed. Additionally, the thick membranes slow the response time of the electrode. While it would be advantageous to place the reference electrode outside the membrane, many problems arising in conjunction with such a configuration have heretofore prevented use of structures of this type.

It has been found that simply placing the reference electrode outside of a hydrophobic membrane causes problems in the operation of the sensor, because of the low electrical conductivity of the hydrophobic membrane due to the fact that ions pass therethrough very slowly. Sensors utilizing more permeable hydrophilic membrane materials, such as cellulose acetate butyrate, enjoy only limited success insofar as such membranes are not very selective in their permeability and hence allow many hydrophilic interfering ions and neutral species therethrough. For example, if an electrode assembly having a hydrophilic membrane were utilized for an analysis of dissolved oxygen in a blood sample, erroneous results could occur owing to interference from ions such as Cu.z or other reducible species which could readily diffuse through the hydrophilic membrane.

As a result of such problems the prior art has heretofore generally disposed working and reference electrodes in polarographic sensors beneath or behind a common membrane. For example U.S. Pat. No. Re. 31,299 discloses an analytical electrode assembly for measuring oxygen concentrations and including working and reference electrodes and electrolyte disposed beneath a common hydrophobic membrane. In addition to the common hydrophobic membrane, the '299 apparatus includes separate ion-selective membrane coatings on the active surfaces of the reference and measuring electrodes. Similarly, U.S. Pat. No. 4,685,465 shows another prior art oxygen sensor having both measuring and reference electrodes disposed behind a single, oxygen permeable membrane.

In an attempt to avoid problems caused by the low electrical conductivity of hydrophobic membranes, various attempts have been made to utilize hydrophilic membranes for electrochemical analyses; however, as mentioned previously, such membranes are not selective in regard to species transmitted therethrough. Pat. No. 4,672,970 describes a measuring electrode having a hydrophilic membrane disposed upon a face thereof and teaches that such hydrophilic materials are superior to, and preferred over hydrophobic materials; however, no attempt is made to deal with problems engendered by the lack of selectivity of such membranes.

It has been found in accord with the present invention that electrode sensor assemblies may be fabricated having working electrodes separated from reference electrodes by hydrophobic membranes provided that the membranes are selected and fabricated to have sufficient ionic conductivity. It has been found in accord with the present invention that hydrophobic membranes may be rendered sufficiently conductive for use in polarographic electrode assemblies by appropriately doping or otherwise modifying the polymeric materials. It has further been found that the membrane is "sufficiently conductive" if its electrical resistance is less than the electrical resistance presented by the remainder of the measuring apparatus. That is to say that the membrane itself should not present the primary limiting step to electrical conduction and hence measurement.

It has also been found that merely rendering the membrane conductive is not sufficient to ensure accuracy in a great many instances. Problems occur because an electrical potential may develop across the hydrophobic membrane owing to different concentrations of ionic species present on either side thereof. This potential adds to the applied working electrode potential and, since it is generally of an unknown magnitude, represents a potential source of error. It has been found, in accord with the principles of the present invention, that this potential can be made to be relatively constant if the membrane is made permeable to a given ionic species known to be present at relatively constant concentrations in all the analyte fluids which will contact the electrode assembly.

It will therefore be appreciated that the present invention solves problems which have heretofore restricted the accuracy, size and fabrication ease of polarographic type electrode assemblies. By the use of the present invention, electrode assemblies may be fabricated having the reference electrodes separated from the measuring electrodes by a selectively permeable, hydrophobic membrane having reasonably high electrical conductivity and manifesting a stable electrochemical potential thereacross in analyte fluids having various ionic compositions therein. These and other advantages of the present invention will be readily apparent from the drawings, discussion, description and claims which are a part hereof.

BRIEF DESCRIPTION OF THE INVENTION

There is disclosed herein an apparatus for measuring the concentration of a chemical species dissolved in an ion containing liquid. The apparatus includes a reference electrode in electrical communication with the liquid; and further includes, a working electrode comprising an electrical conductor having a portion thereof electrochemically active with the dissolved species and a continuous, hydrophobic membrane, permeable to the chemical species, disposed so as to separate the active portion of the working electrode from the sample liquid and from the reference electrode. The apparatus preferably includes a body of electrolyte material disposed upon at least the active portion of the working electrode and covered by the membrane. The electrolyte may be a developed electrolyte generated as a result of natural hydration and/or electrochemical reactions at the interface between the hydrophobic membrane and the electrode. In other instances, the electrolyte may be separately provided.

In one preferred embodiment the electrical resistance of the membrane should be less than the electrical resistance of the remainder of the electrical circuitry disposed between the working electrode and the reference electrode. It is further preferred in some instances that the membrane be an ionic conductor, at least partially permeable to a preselected ionic species found in the sample liquid or calibration liquid; and toward that end, the membrane may include an ionophore or ion-exchange species therein. In other instances, conductivity may be achieved by utilizing a membrane fabricated from a graft copolymer of a hydrophobic polymeric material having ion conducting segments therein.

DETAILED DESCRIPTION OF THE INVENTION

Figure 2:
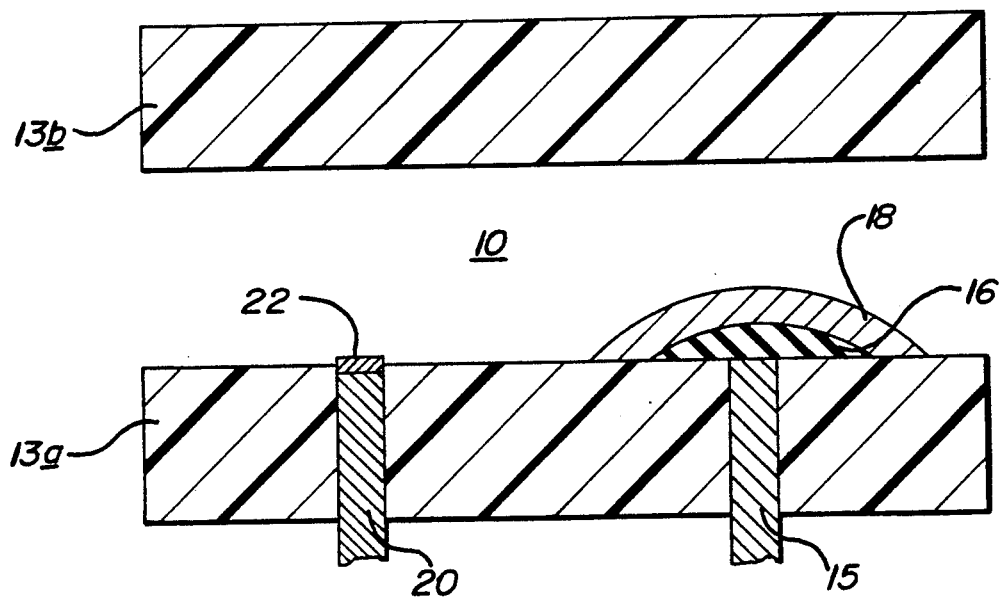
FIG. 2 is a cross-sectional view of one embodiment of electrode assembly of the present invention comprised of a reference and measuring electrode separated by a hydrophobic membrane.

Referring now to FIG. 2, there is shown a cross-sectional view of one particular apparatus structured in accord with the principles of the present invention and operative to electrochemically measure the concentration of a dissolved chemical species in a body of fluid. As used herein the term "chemical species" is inclusive of dissolved gases and other neutral species as well as ions and radicals. The apparatus of FIG. 2 is comprised of a fluid flow channel 10 defined by two portions 13a, 13b of an insulating body. The insulating body and channel 10 defined thereby may be a portion of an electroanalytical apparatus such as a blood gas monitor and may be operative to pass a stream of fluid through the channel 10 in either a continuous or periodic manner. It is to be understood, that the principles disclosed herein may be similarly applied to various apparatus and various electrode configurations.

Disposed within the fluid flow channel is a working electrode which includes an electrical conductor 15, at least a portion of which is electrochemically active toward the dissolved species being analyzed. By "electrochemically active" it is meant that the electrode material is capable of transferring electrons to, or removing electrons from, the species being analyzed, such transfer of electrons being accomplished by creating a potential between the working conductor 15 and the electrolyte layer 16. In the illustrated embodiment, the conductor 15 is shown as disposed within, and supported by, the lower portion 13a of the insulating body such that one face of the conductor 15 is exposed to the fluid flow channel 10.

Disposed atop this exposed face of the conductor 15 is a body of electrolyte material 16, the function of which is to provide a medium in which contact between the species being analyzed and the conductor 15 can occur. As will be discussed in greater detail hereinbelow, there are a wide variety of electrolyte materials available for practice of the present invention and choice of such materials will depend upon the particular species being analyzed, compatibility with remaining materials of the electrode assembly, and other such factors. In many instances it is desirable to employ a jelled or otherwise thickened electrolyte material and in some instances this material may be deposited as a dehydrated, rehydratable electrolyte to facilitate fabrication, storage and handling of the electrode assemblies. In such instance, rehydration will take place during or immediately prior to use. The preparation and use of dehydrated, rehydratable electrolyte compositions, is disclosed in U.S. Pat. 3,878,830 and 3,999,284; the disclosures of which are incorporated herein by reference. In yet other instances, the electrolyte 16 may be a "developed electrolyte" and such term is meant to refer to an electrolyte which is not specifically added, but which forms or develops from ions present in the membrane or on the surface of the conductor 15 or insulating body 13a and/or as a result of an electrochemical reaction of the analyte with the surface of the electrode. In yet other instances, the electrolyte 16 may be a polymeric, ionic material such as Nafion.

Disposed atop and completely covering all of the body of electrolyte material 16, is a membrane 18 which is a hydrophobic membrane, permeable to the species which is being analyzed. As will be explained in greater detail hereinbelow, membrane 18 also has permeability to preselected ionic species and is of sufficiently high electrical conductivity to permit polarographic analyses to take place. In general, it has been found that the electrical conductivity of the membrane 18 should be such that any electrical resistance presented thereby is smaller than the electrical resistance of the remainder of the analytical system. The membrane 18 and its properties will be described in greater detail hereinbelow.

The apparatus of FIG. 2 further includes a reference electrode 20 disposed in a spaced apart relationship with the working electrode assembly, but in electrical communication with the fluid in the fluid flow channel 10. The reference electrode 20 is also supported in the lower portion 13a of the insulating body and is disposed such that at least a portion thereof is in electrical communication with the fluid in the fluid flow channel 10. As depicted in FIG. 2, one face 22 of the electrical conductor 20 comprising the reference electrode is disposed to contact the fluid. This fluid contacting face 22 may be of a different composition than the remainder of the body of the reference electrode 20. For example, the body of the electrode 20 may be fabricated from silver and the face 22 thereof may be a silver chloride coating thereupon. As is well known to those of skill in the art, the face 22 of the electrode 20 may be protected by a body of hydrophilic or hydrophobic membrane material and/or may have another coating thereupon. If the membrane is hydrophobic, then it should be doped with an appropriate ionophone.

In operation, a sample fluid containing an analyte is disposed within the fluid flow channel 10 and an electrical potential applied between electrodes 15 and 20. For example, in the case of analysis for oxygen content, the working electrode 15 is made negative with respect to the reference electrode 20 and consequently molecular oxygen is reduced at the face thereof to hydrogen peroxide and/or hydroxide ions. The reference electrode 20 is maintained at a positive potential with respect to the working electrode and current flow therebetween occurs as a result. The magnitude of this current is proportional to the oxygen concentration.

There are many configurations in which electrodes of this type may be employed. The FIG. 2 embodiment represents an arrangement in which a sample of fluid to be analyzed is flowed through a channel in which it interfaces with the measuring and reference electrodes. This particular embodiment is well suited for use in an in-line blood gas analyzer. It may also be utilized for testing of other fluids in a flow-through mode. By the appropriate choice of materials for the reference electrode, working electrode, electrolyte and membrane, apparatus for measuring a wide variety of dissolved species may be constructed.

Figure 3:
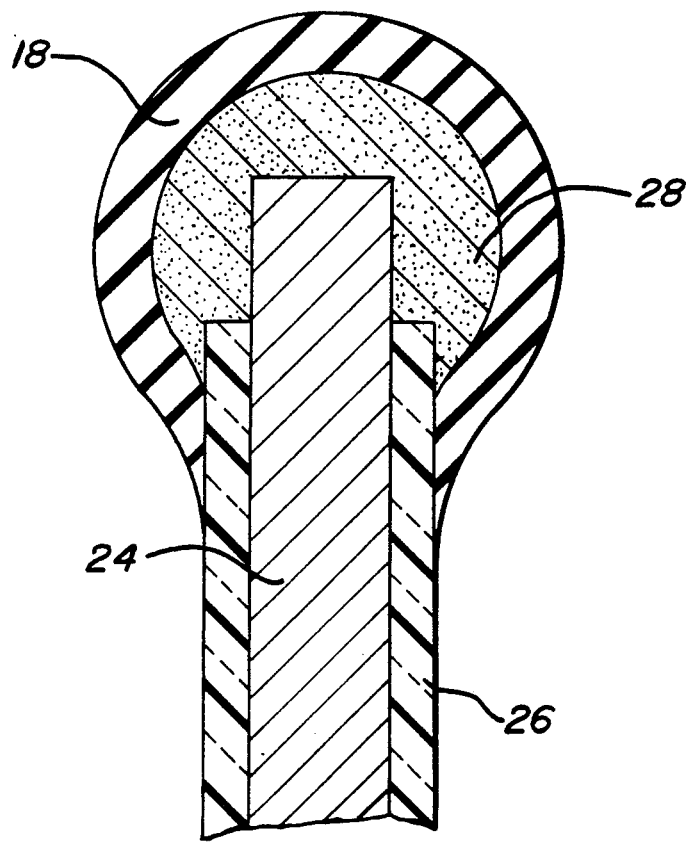
FIG. 3 is a cross-sectional view of a particular electrode structured in accord with the principles of the present invention.

Referring now to FIG. 3, there is shown yet another electrode structured in accord with the principles disclosed herein. In contrast to the planar electrode of FIG. 2, the FIG. 3 electrode is of an elongated probe design making it particularly well suited for immersion into the sample fluid. The particular electrode of FIG. 3 includes a conductive member 24, electrochemically active with the chemical species being analyzed. A portion of the conductor 24 is protected by an electrically insulating material forming a sheath 26, thereabout. This electrical insulator may be selected from any one of the many commercially available materials such as rubber, synthetic polymeric material such as fluorocarbon polymers, vinyls, acetates and the like. The insulating sheath 26 is disposed about only a portion of the conductor 24 so as to leave an exposed portion thereof. This exposed portion has a body of electrolyte material 28 in contact therewith and generally similar to the electrolyte material previously described. Surrounding the electrolyte material 28 is the hydrophobic membrane 18, which cooperates with the insulating sheath 26 to seal the electrolyte material 28 about the exposed portion of the conductor 24.

The FIG. 3 electrode may be readily fabricated by stripping insulation from a portion of a conductive wire;

dipping the exposed portion of the conductor in an electrolyte mixture; (optionally, drying the electrolyte) and dipping the electrolyte coated member into a solution of the membrane polymer. Electrodes of this configuration may be made in a miniature form which makes them ideally suited for intra-venous or intra-arterial measurements. Although not illustrated, these electrodes will need to be utilized in conjunction with an appropriate reference electrode.

The membrane 18 is a critical element of the electrode assembly of the present invention. As mentioned hereinabove, the membrane should be hydrophobic. This is in contradistinction to hydrophilic membranes utilized in many prior art electrode assemblies. Hydrophilic membranes manifest permeability to a wide variety of neutral and ionic species and hence can cause problems of accuracy and can give erroneous readings. While hydrophobic membrane materials are known and have been heretofore employed, the previously available membranes were of low electrical conductivity owing to poor ionic passage therethrough. This low conductivity necessitated placement of both reference and working electrodes beneath or behind a single membrane if reasonable response times and accurate measurements were to be made.

It has generally been found in accord with the principles of the present invention that the electrical resistance of the hydrophobic membrane should be less than the resistance of the remainder of the measuring circuit; that is to say, the limiting electrical resistance should not be presented by the membrane.

Since in most cases, analytical apparatus is typically fabricated with relatively small area micro electrodes, electrical resistance of the remainder of the circuit will depend strongly upon the area of the working electrode utilized. Hence, a wide range of membrane resistances may be employed while still keeping below the resistance of the remainder of the circuit. While the present invention may be practiced with any membrane having an electrical resistance less than the electrical resistance of the remainder of the measuring circuit, it has generally been found that for most practical purposes membrane resistances will typically range between approximately $10^4$ and $10^7$ ohms.

There are a wide variety of hydrophobic materials which may be employed for the fabrication of the membranes. Included are various fluorocarbons such as polytetrafluoroethylene, polyvinylidene fluoride, and the like, as well as other materials such as silicone polymers, polyethylene, polypropylene, poly(vinyl chloride) and the like. Conductivity may be imparted to such membrane materials, in some instances, by doping them with appropriate conductivity enhancing materials. Ionophores have been found to be particularly advantageous in imparting ionic conductivity to hydrophobic membranes. Ionophores may be generally described as compounds which facilitate ion transport through a membrane and may be selected from materials which specifically bind particular ionic species. For example, it is known that valinomycin exerts preferential binding for potassium ions. Similarly, various cyclic polyethers are known to selectively bind sodium, potassium or other alkaline metal ions. Various compounds of monensin have also been shown to bind sodium ions. Techniques of fabricating ion-selective membranes by incorporation of appropriate compounds therein are well-known to those of skill in the art and reference thereto may be found in many publications, including U.S. Pat. Nos. 4,214,968 and 3,562,129, the disclosures of which are incorporated herein by reference.

Membrane conductivity may also be enhanced by the addition of ion-exchange compounds thereto. Such compounds and their use in the fabrication of conductive membranes is well-known to those of skill in the art and will be found with reference to, inter alia, the above referenced patents. Quaternary ammonium compounds are one particular group of ion-exchange species which may be readily incorporated into membranes, and organic sulfonates are another.

Appropriate ionic conductivity may also be achieved by utilizing a membrane fabricated from a graft copolymer. Materials of this type comprise a first polymeric material having portions of a second material grafted thereupon at various locations along the length of the primary polymeric chain. By appropriate choice of the grafted segments some limited and selective ionic permeability may be achieved in a membrane which would otherwise be of low permeability and low conductivity. Graft polymers and methods for their manufacture are well known to those of skill in the art and will not be elaborated upon herein.

Figure 1:
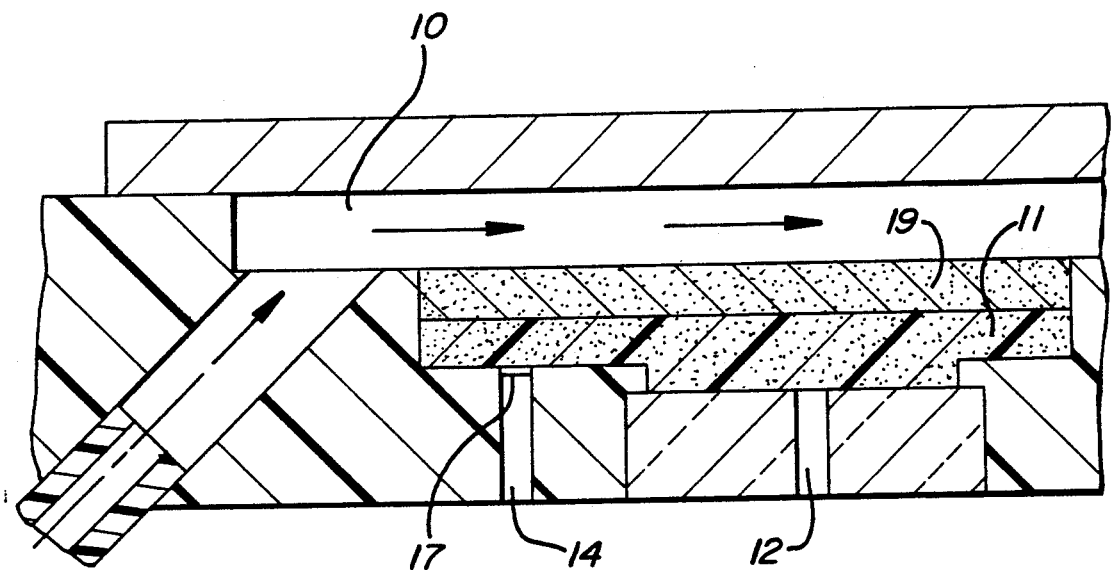
FIG. 1 is a cross-sectional view of a prior art electrode assembly showing a reference and measuring electrode disposed beneath a single, continuous, hydrophobic membrane.

In order for a polarographic electrode to maintain stable calibration characteristics, the applied potential between the working and reference electrodes must be held within fairly narrow limits. This is to assure that the potential between the electrolyte solution and working electrode, which actually drives the reaction is constant. In a prior art electrode assembly such as that of FIG. 1, the two electrodes are in the same electrolyte solution disposed beneath a protective membrane, and maintaining a constant potential is no problem.

In the present invention, a membrane (of limited permeability) and the external solution are interposed between the working and reference electrodes. New potentials are created between the membrane and the differing solutions on either side of it. These potentials will add to the applied potential between the working electrode and reference electrode complicating the measurement. Furthermore, these potentials will change as the relative compositions of the solutions change; since the magnitude of these potentials will be unknown and generally changing, they can provide a significant source of error in measurement.

The present invention presents a solution to this problem by modifying the membrane so that the trans-membrane potential will be relatively constant for the range of solutions likely to be encountered. This constant potential may then be readily accommodated by the measuring circuitry. A relatively constant membrane potential can be maintained by making the membrane permeable to a particular ionic species found at a relatively fixed concentration in the expected range of sample fluids. For example, in the case of a sensor for measuring blood-oxygen levels, the membrane is made selectively permeable to sodium ions. The concentration of this ion in blood (and calibration fluids used with the sensor) falls within a narrow range; consequently, the membrane potential will not be altered by more than a few millivolts when shifting between solutions. The small shift in polarization potential occasioned thereby is not sufficient to cause any noticeable error in the measurement of oxygen concentration.

As mentioned hereinabove, the electrolyte material disposed between the working electrode and the hydrophobic membrane may comprise a variety of compositions, the primary criterion being that the electrolytes be capable of transporting the species being analyzed so as to allow its electrochemical reaction at the working electrode face. In general, the electrolyte will include ions such as sodium, potassium, chloride, bicarbonate and the like. It may further include thickening and/or conditioning materials. In some instances, the electrolyte may be a developed electrolyte; in other instances the electrolyte may be applied in a dry form, or applied as a liquid solution which is subsequently allowed to dry, thereby providing for a dehydrated electrode. Dehydrated electrodes allow for long term storage and may be readily rehydrated by immersion in an appropriate aqueous solution prior to use.

There are a wide variety of conductive materials which may be employed in the fabrication of the present electrodes. It is generally preferred that the conductive material of the working electrode be inert to the electrolyte and the species being measured and toward this end it has been found that platinum or gold electrodes are particularly advantageous. Depending upon the analytical environment, less costly materials such as stainless steel, carbon or plated materials may in some instances be readily substituted by one of skill in the art.

In addition to direct sensing of dissolved species, the electrodes of the present invention may be utilized in an indirect manner for the measurement of dissolved species which are not primarily electrochemically reactive at the electrode face. For example, it is frequently desirable to measure the concentration of various molecules such as glucose in a blood stream. In one particular measurement methodology, glucose is analyzed by the use of an electrode including a body of the enzyme, glucose oxidase, which in the presence of oxygen, converts glucose to gluconic acid and hydrogen peroxide. Glucose is measured by detecting the generated hydrogen peroxide or by measuring the depletion of oxygen; in some instances the concentration of the gluconic acid byproduct is measured. Such measurement techniques are well-known to those of skill in the art; however, they have not been heretofore implemented in conjunction with electrode assemblies of the type disclosed herein.

Figure 4:
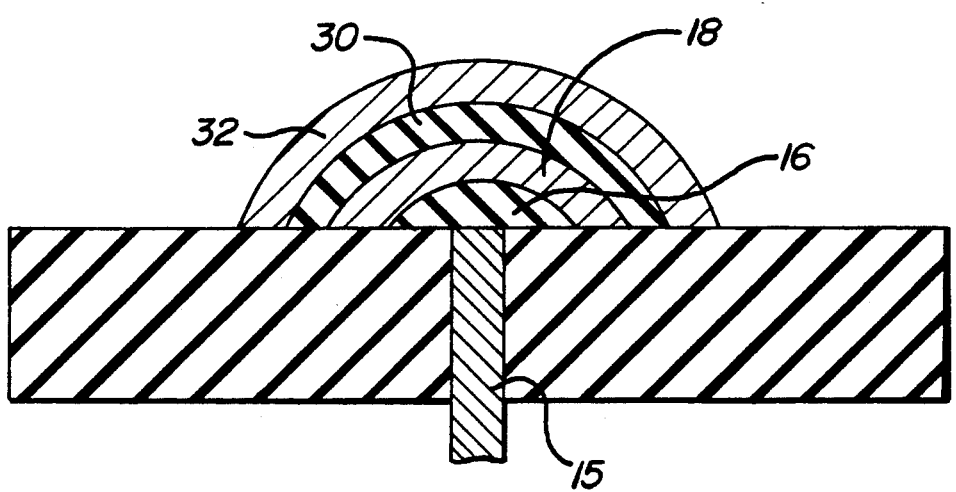
FIG. 4 is a cross-sectional view of a first enzyme containing sensor electrode structured in accord with the principles of the present invention.

FIG. 4 depicts a cross-sectional view of one embodiment of an enzyme containing measuring electrode structured in accord with the principles of the present invention and as particularly configured to measure the concentration of glucose in a fluid sample. The electrode assembly of FIG. 4 builds upon the sensor technology described with reference to FIG. 2 and as such, is utilized in conjunction with a reference electrode (not illustrated).

The electrode assembly of FIG. 4 includes a conductor 15, an electrolyte 16 and an inner, hydrophobic membrane 18, all generally similar to those previously described. The electrode structure of FIG. 4 further includes a body of enzyme material 30 disposed atop the hydrophobic membrane 18. The composition and concentration of the enzyme will depend upon the species being analyzed; and, in the case of glucose, one preferred enzyme is glucose oxidase. The enzyme layer 30 may be of various forms known in the art such as a polymeric material crosslinked with the enzyme, a solution of enzyme material or in some instances, enzyme bonded to the material forming one of the membranes 18,32 of the sensor.

The enzyme layer 30 is preferably protected with an exterior membrane 32 which may be either a hydrophilic or a hydrophobic membrane The external membrane 32 should have a reasonably good permeability for the species being analyzed as well as for any other species ancillary to the analysis. For example, in the case of the glucose analysis, the membrane 32 should be permeable to both glucose and oxygen. As mentioned previously, it is important to maintain a stable electrochemical potential and towards that end, the outer membrane 32 and the inner membrane 18, should be permeable to the appropriate ion employed to maintain a constant polarization potential in the circuit.

The electrode assembly of FIG. 4 is a glucose measuring electrode operating in a mode wherein oxygen depletion is measured. The hydrophobic membrane 18, electrolyte 16 and polarity of the working conductor 15 are all optimized to measure oxygen concentration. In this sensor, glucose and oxygen react in, or at, the enzyme layer 30; oxygen diffuses through the hydrophobic membrane 18 and the concentration of oxygen is measured as in the foregoing examples. The background concentration of oxygen in the fluid sample being analyzed is measured by a separate electrode system, preferably one similar to that of FIGS. 2 or 3. By comparison of the background oxygen level with the oxygen level beneath the enzyme layer, depletion of oxygen and hence concentration of glucose is determined.

Figure 5:
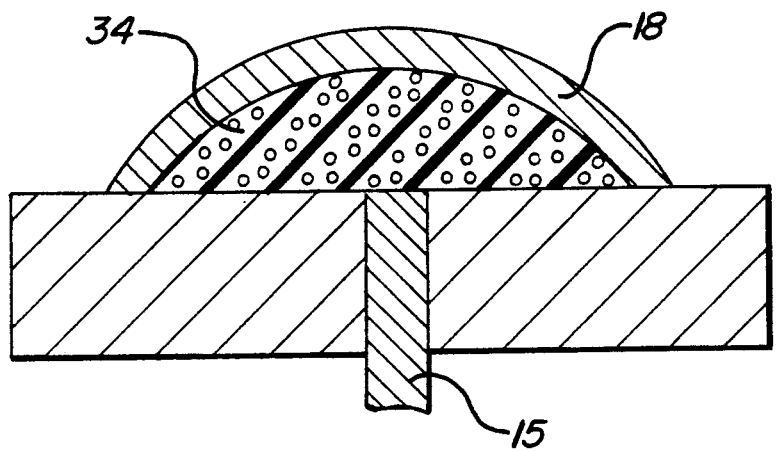
FIG. 5 is a cross-sectional view of another enzyme containing sensor electrode structured in accord with the principles of the present invention.

Other configurations of enzyme containing sensors may be fabricated in accord with the principles of the present invention. Referring now to FIG. 5, there is shown another such sensor assembly. This particular sensor includes a working electrode 15 and an external, hydrophobic membrane 18, both of which are generally similar to those previously described. The sensor of FIG. 5 further includes a body of electrolyte material 34 which includes an enzyme material therein. The membrane 18 has selective ionic permeability so as to maintain a stable electrochemical potential and toward that end includes an ionophore or ion exchange species, or is fabricated from a copolymer as previously described. The membrane 18 must also be permeable to the species being analyzed, in this instance glucose. The electrolyte layer 34 includes glucose oxidase or a similar enzyme. The sensor of FIG. 5 may operate in either an oxygen detection mode, wherein depletion of oxygen resultant from the oxidation of glucose is measured, or a peroxide detection mode, wherein hydrogen peroxide resulting from the enzymatic reaction is measured. In those instances where peroxide is being detected, the working conductor 15 will be maintained at a positive potential so as to oxidize the peroxide. In those instances where the sensor of FIG. 5 is operated in an oxygen sensing mode, a separate, oxygen sensitive electrode will be needed to establish a base oxygen concentration. Obviously, the sensor of FIG. 5 will be utilized in combination with an external reference electrode.

Figure 6:
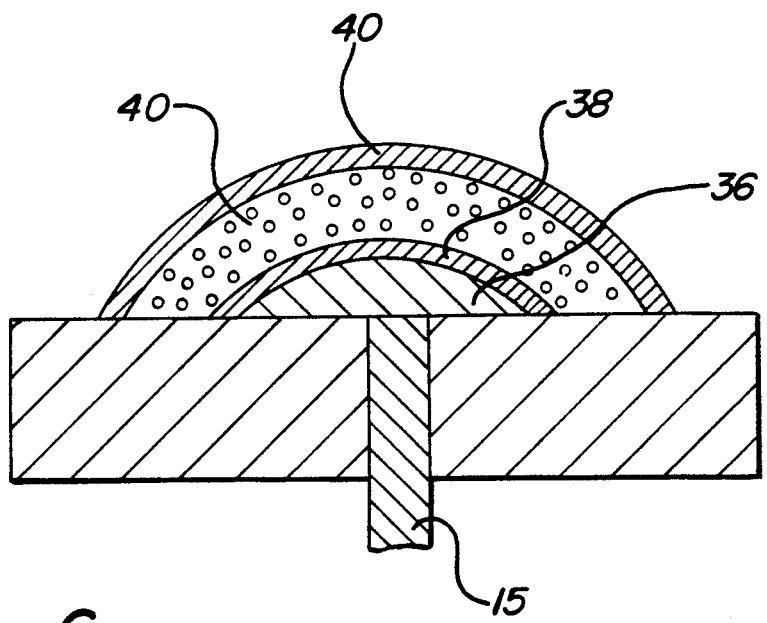
FIG. 6 is a cross-sectional view of yet another enzyme containing sensor electrode structured in accord with the principles of the present invention.

Referring now to FIG. 6, there is shown yet another embodiment of enzyme containing a sensor. The sensor of FIG. 6 is operative to sense the concentration of glucose and does so in a hydrogen peroxide detection mode of operation. A working conductor 15 has a first body of electrolyte material 36 retained in contact therewith by a first membrane 38. Disposed atop the first membrane 38 is a body of enzyme material 40 which is protected by an outer membrane 42. In operation, glucose passes through the first membrane 42, is oxidized by the enzyme in the enzyme containing layer 40 and the hydrogen peroxide produced by the oxidation passes through the second membrane 38 and is oxidized at the working conductor 15. The first membrane 38 and/or the outer membrane 42 must be a hydrophobic membrane which has an appropriate ionic permeability to allow for maintenance of a stable electrochemical potential as previously mentioned. Additionally, the first membrane 38 must be permeable to hydrogen peroxide and the outer membrane 42 must be permeable to glucose. Within these broad parameters, it is to be appreciated that a variety of glucose sensors operating in a hydrogen peroxide detection mode may be fabricated. As in the foregoing examples, the sensor of FIG. 6 will be utilized in combination with an external reference electrode.

Still other modifications of the foregoing structures may be utilized in the fabrication of sensors. For example, with respect to glucose measurements, the approach described hereinabove is not limited to cases where oxygen is the co-substrate in the enzyme reaction and hydrogen peroxide is a by-product thereby.

There has developed a body of technology relating to the use of metallocenes as mediators or electron transfer agents in enzymatic electroanalytical sensors. For example, ferrocene and its derivatives have been utilized to assist in the enzyme mediated oxidation of glucose, and such techniques are disclosed in U.S. Pat. No. 4,711,245, the disclosure of which is incorporated herein by reference. As is disclosed therein, glucose may be readily reacted with glucose oxidase or glucose dehydrogenase in the presence of ferrocene derivatives. Use of such mediating agents eliminates the need for oxygen thereby simplifying the analysis. This metallocene based technology may be readily adapted for use in connection with the present invention by the simple expedient of incorporating appropriate metallocene reagents within the sensor structure. For example, the structure of FIG. 5 can be modified to include ferrocene in the enzyme containing layer 34.

Other modifications of the present invention may be similarly implemented. By selection of appropriate membranes and/or enzymes, species other than oxygen and glucose may be measured. For example, lactate ion may be readily sensed as may a variety of other organic and inorganic species. It will be appreciated that a great variety of electrode configurations may be fabricated in accord with the principles of the present invention by utilizing conductive, hydrophobic membranes. The present invention allows placement of a reference electrode external of a working electrode thereby permitting use of thinner electrolyte layers and saving space and fabrication steps. The membrane of the present invention is of limited permeability but has sufficient electrical conductivity to not present a limiting resistance in the measurement circuit and has a preselected ionic permeability to a species selected to provide a relatively constant membrane potential. Electrodes structured in accord with the principles of the present invention may be fabricated to sense a variety of substances and may further include enzymes or other reactive materials to allow measurement of species not directly active electrochemically.

Fabrication of the electrode assemblies is relatively simple; a body of conductive material, such as a length of gold or platinum wire is typically embedded in an electrically insulating support member such as a glass disk or a polymeric body; in some instances the conductor is an insulated wire. A portion of the conductor, free of any insulating material, is exposed and a body of electrolyte material is placed thereatop. This electrolyte material may be in the form of a solution or it may be a dehydrated material as noted previously. The hydrophobic membrane is subsequently applied over the body of electrolyte material and this may be readily accomplished by dipping the electrode assembly into a solution of membrane material or by dropping the solution thereonto. In some instances it is preferable to dehydrate the electrolyte prior to coating a membrane material whereas in other instances the membrane material and its solvent are such that coating of the solvent solution onto a wet electrolyte layer may be carried out. In the case of enzyme containing electrodes, such materials will obviously be added as appropriate. In yet other instances, the electrolyte may be a developed electrolyte, and hence, no specific electrolyte material is applied to the electrode during fabrication. The electrochemical sensors of the present invention may be readily incorporated in a variety of configurations such as single and multiple sensor units, flow-through sensors as well as probe-type or planar sensors.

In light of the foregoing, it is apparent that many modifications and variations of the electrode assembly of the present invention may be made in keeping with the teaching herein. Accordingly, the foregoing drawings, description and discussion are merely meant to be illustrative of particular embodiments of the present invention and not limitations upon the practice thereof. It is the following claims, including all equivalents, which define the scope of the present invention.

We claim:

1. An apparatus for measuring the concentration of a chemical species dissolved in an ion containing sample liquid, said apparatus including:
   A) a reference electrode in electrical communication with the sample liquid;
   B) a working electrode comprising:
      an electrical conductor having a portion thereof electrochemically active with the dissolved species;
   C) means for measuring the flow of electrical current between the working electrode and the reference electrode; and
   D) a continuous, hydrophobic membrane, permeable to both said dissolved species and to the ion contained in said liquid, said membrane having an electrical resistance lower than the electrical resistance of the electrical conductor of the working electrode and the means for measuring the flow of electrical current, said membrane, disposed so as to separate the active portion of the working electrode from the sample liquid and from the reference electrode.

2. An apparatus as in claim 1, further including a body of electrolyte material disposed upon at least the active portion of the conductor, said electrolyte material covered by the membrane.

3. An apparatus as in claim 2, wherein said electrolyte is a developed electrolyte.

4. An apparatus as in claim 2, wherein said electrolyte is a polymeric electrolyte.

5. An apparatus as in claim 2, wherein said electrolyte is a dehydrated electrolyte and the membrane is at least partially permeable to water.

6. An apparatus as in claim 1, wherein the membrane is an ionic conductor at least partially permeable to a preselected ionic species in the liquid.

7. An apparatus as in claim 1, wherein said membrane is doped with an ionophore.

8. An apparatus as in claim 1, wherein said membrane is doped with an ion-exchange species.

9. An apparatus as in claim 8, wherein said ion-exchange species is a quaternary ammonium compound.

10. An apparatus as in claim 8, wherein said ion-exchange species is an organic sulfonate.

11. An apparatus as in claim 1, wherein said membrane is fabricated from a graft copolymer of a hydrophobic polymeric material having ion conducting segments therein.

12. An apparatus as in claim 1, wherein said membrane is fabricated from a material selected from the group consisting of: silicone polymers, fluorocarbon polymers, poly(vinyl chloride), polyethylene, polypropylene and combinations thereof.

13. An apparatus as in claim 1, wherein said reference electrode is a silver electrode having a coating of silver halide upon at least a portion thereof.

14. An apparatus as in claim 1, wherein said active portion of the working electrode comprises a body of platinum.

15. An apparatus as in claim 1, wherein said hydrophobic membrane is permeable to oxygen.

16. An apparatus as in claim 1, further including a body of enzyme material.

17. An apparatus as in claim 16, wherein said body of enzyme material includes a metallocene therein.

18. An apparatus as in claim 17, wherein said body of enzyme material is disposed atop at least a portion of the hydrophobic membrane.

19. An apparatus as in claim 18, wherein said enzyme is covered by an outer membrane.

20. An apparatus as in claim 17, wherein said body of enzyme material is disposed beneath said hydrophobic membrane.

21. An apparatus as in claim 17, wherein said enzyme is catalytic of chemical reactions between glucose and oxygen.

22. An electrode assembly for measuring the concentration of a chemical species dissolved in an ion containing liquid, said assembly including:
a fluid channel bounded by at least one wall and operative to retain the liquid therein;
a reference electrode disposed so as to have at least a portion thereof exposed in said channel;
a working electrode comprising an electrically insulating support member, an electrical conductor supported by said support member and having an active portion thereof projecting from said support member, said support member disposed in the fluid channel so that the active portion of the conductor is exposed therein;
a body of electrolyte material disposed upon the support member and covering the active portion of the electrical conductor;
means for measuring the flow of electrical current between the working electrode and the reference electrode; and
a continuous, hydrophobic membrane permeable to both the dissolved chemical species and the ion contained in said liquid, said membrane having an electrical resistance lower than the electrical resistance of the electrical conductor of the working electrode, the body of electrolyte material and the means for measuring the flow of electrical current, said membrane disposed so as to cover the electrolyte material and thereby separate said electrolyte material and the active portion of the electrode from the liquid and from the reference electrode.

23. An apparatus for measuring the concentration of a chemical species dissolved in an ion containing sample liquid, said apparatus including:
A) a reference electrode in electrical communication with the sample liquid;
B) a working electrode comprising:
an electrical conductor having a portion thereof electrochemically active with the dissolved species;
C) means for measuring the flow of electrical current between the working electrode and the reference electrode;
D) a continuous, hydrophobic membrane, permeable to both said dissolved chemical species and the ion contained in said liquid, said membrane manifesting ionic conductivity and having an electrical conductivity in the range of $10^4$ and $10^7$ ohms and an electrical resistance less than the electrical resistance of the electrical conductor of the working electrode and the means for measuring the flow of electrical current, said membrane disposed so as to separate the active portion of the working electrode from the sample liquid and from the reference electrode; and
E) a body of electrolyte material disposed upon at least the active portion of the conductor, said electrolyte material covered by the membrane.

* * * * *